United States Patent [19]
Takizawa et al.

[11] 4,102,565
[45] Jul. 25, 1978

[54] SLIT LAMP MICROSCOPE

[75] Inventors: Shiro Takizawa, Tokyo; Shinichi Nishimura, Ageo, both of Japan

[73] Assignee: Tokyo Kogaku Kikai Kabushiki Kaisha, Tokyo, Japan

[21] Appl. No.: 703,547

[22] Filed: Jul. 8, 1976

[30] Foreign Application Priority Data

Jul. 10, 1975 [JP] Japan .............................. 50-96021[U]

[51] Int. Cl.² .............................................. A61B 3/10
[52] U.S. Cl. .................................. 351/14; 350/96.10; 351/7; 351/16
[58] Field of Search .................... 351/7, 14, 16, 24

[56] References Cited
U.S. PATENT DOCUMENTS 3,068,745  12/1962  Peck ..................................... 351/14 X
3,414,348  12/1968  Gambs ................................... 351/24
3,652,153  3/1972  Gambs ................................... 351/14

*Primary Examiner*—Paul A. Sacher
*Attorney, Agent, or Firm*—Stevens, Davis, Miller & Mosher

[57] ABSTRACT

A slit lamp microscope includes an illumination light source from which light is passed through two separate optical paths to the patient's eye. The first of the optical paths includes a slit mask and a projecting lens so that the light is focused on the patient's eye to provide a bright slit-like illumination. The light which has passed through the second path provides a uniform auxiliary illumination around the illuminated slit area so that the location of the area can be readily determined with respect to other portions of the patient's eye.

5 Claims, 4 Drawing Figures

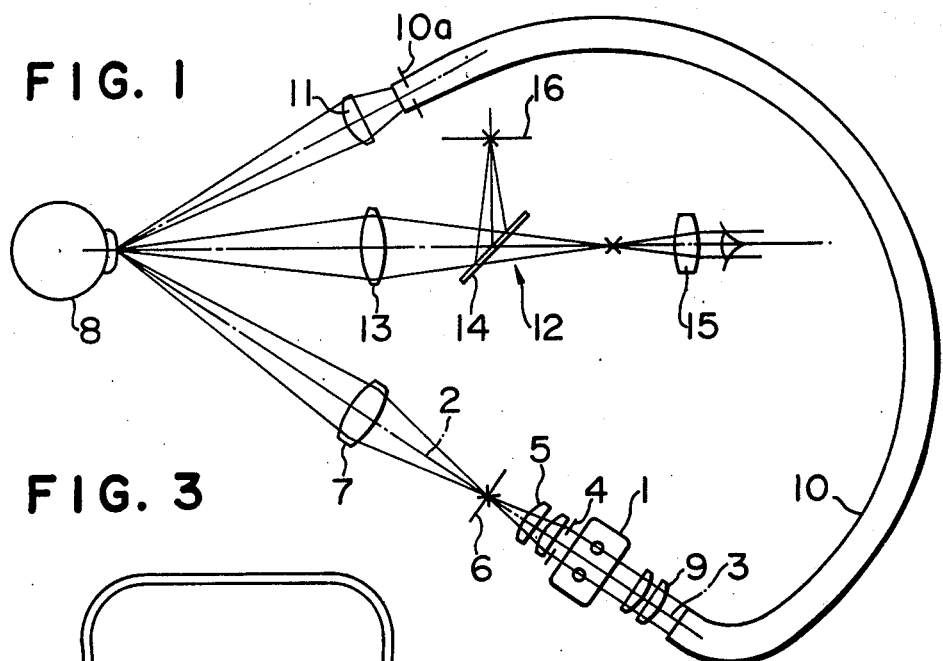
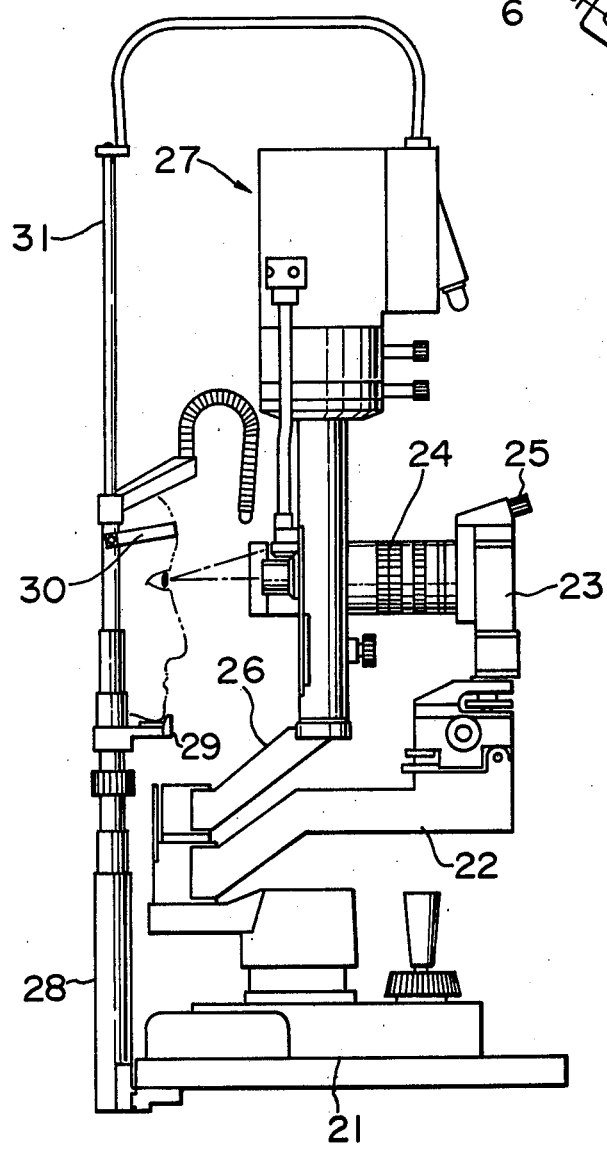

SLIT LAMP MICROSCOPE

FIELD OF THE INVENTION

The present invention relates to slit lamp microscopes and more particularly to slit lamp microscopes having means for providing auxiliary illumination around the illuminated slit area.

BACKGROUND OF THE INVENTION

In slit lamp microscopes investigating eye diseases, it has already been proposed to provide uniform illumination around the illuminated slit area so that the position of the slit area can readily be determined with respect to other portions of the eye being investigated. Most conventionally, there has been provided, in addition to the light source for the slit illumination, a separate light source for the auxiliary uniform illumination. However, the arrangement has been found disadvantageous in that it requires two separate light sources which, as a matter of course, increases the manufacturing cost and requires troublesome handling of the components.

In order to eliminate the above disadvantage, there has been proposed in Japanese utility model publication Sho 47-27558 the use of a light diffusing plate having a transparent slit area. However, this proposal has also been found to be disadvantageous in that only a limited bundle of light is allowed to pass through the transparent slit area and therefore the brightness of the slit illumination is decreased.

OBJECTS OF THE INVENTION

The present invention has a primary object to eliminate the above disadvantages of the prior art and to provide a slit lamp microscope having a single light source which can provide a slit illumination with a high degree of brightness as well as uniform auxiliary illumination around the illuminated slit area.

Another object of the present invention is to provide a slit lamp microscope which has means for providing auxiliary uniform illumination but is less expensive to manufacture and more convenient to use.

SUMMARY OF THE INVENTION

According to the present invention, the above and other objects can be accomplished by a slit lamp microscope comprising a light source, a first optical path for directing light from said source through slit means to the patient's, eye, a second optical path for directing light from said source to said patient's eye so as to provide uniform auxiliary illumination, and optical means defining a microscope for investigating the patient's eye. Preferably, optical lens means is provided in said first optical path so that the light through the path is focused onto the patient's eye so as to provide a bright slit illumination. The microscope in accordance with the present invention may be associated with photographing means for taking a picture of the patient's eye. In such an arrangement, the light source may be provided for photographing at a position conjugate with a second light source with respect to lens means disposed between the light sources.

BRIEF DESCRIPTION OF THE DRAWINGS

The above and other objects and features of the present invention will become apparent from the following descriptions of the preferred embodiments when considered in conjunction with the accompanying drawings, in which:

FIG. 1 is a diagrammatical plan view of the optical system of the slit lamp microscope in accordance with one embodiment of the present invention;

FIG. 3 is a side view of the microscope in accordance with another embodiment of the present invention; and, FIG. 4 is a view showing the illuminating arrangement employed in the microscope shown in FIG. 3.

DETAILED DESCRIPTION OF THE ILLUSTRATED EMBODIMENTS

Figure 2:
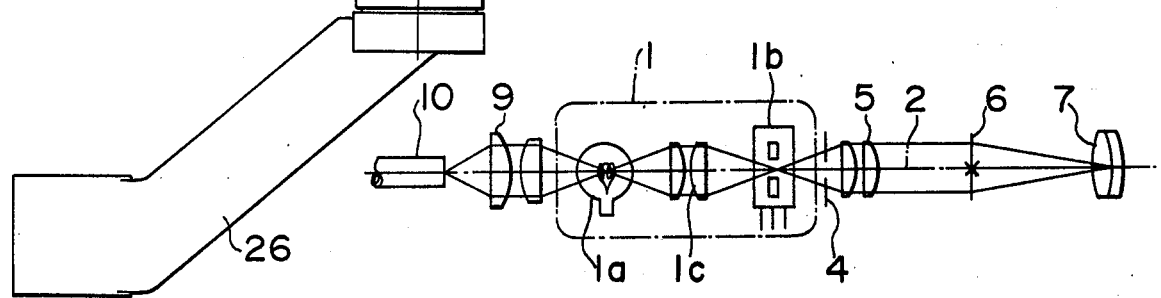
FIG. 2 is a detailed view of the light source used in the microscope shown in FIG. 1.

Referring now to the drawings, particularly to FIGS. 1 and 2, there is shown an optical system for a slit lamp microscope. The system includes light source means 1 from which light is passed through a first optical path 2 and a second optical path 3. In the optical path 2, there are disposed an iris 4, a condenser lens 5, a slit mask 6, and a projecting lens 7 so that the light from the source 1 is focused by the lens 7 onto the patient's eye 8 in the form of a slit.

In the optical path 3, there are disposed a condenser lens 9, a light guide 10, and a condenser lens 11 so that the light from the source 1 is directed through the path 3 to the patient's eye 8 so as to provide uniform illumination around the illuminated slit area. The light guide 10 may be provided with an adjustable iris 10a so that the intensity of the uniform illumination can be adjusted as desired.

The optical system is further provided with a microscopic section 12 which includes an object lens 13, a translucent mirror 14, and an eye lens 15. The translucent mirror 14 allows the light from the object lens 13 to partially pass therethrough but reflects the remainder of the light toward a photographic film 16.

FIG. 2 shows the detailed arrangement of the light source means 1. Referring to FIG. 2, it will be seen that the light source means 1 includes a light source 1a, such as a tungsten lamp and a photographing lamp, 1b, such as a xenon lamp. Between the light sources 1a and 1b, there is disposed a lens 1c. The arrangement is such that the light sources 1a and 1b are conjugate with each other with respect to the lens 1c.

The light sources 1a and 1b may be disposed in exact alignment with the optical axis 2 or may be slightly offset therefrom. Since the xenon lamp 1b includes a pair of opposed electrodes, it may be disposed on the optical path 2, without forming any obstacle in the path 2, in such a manner that the light from the lamp 1a is focused at the gap between the paired electrodes of the xenon lamp 1b.

In use, only the lamp 1a is energized for visual investigation so that the light from the lamp 1a, is, on one hand, passed along the path 2 to the patient's eye 8 so as to illuminate it in the form of a slit, and on the other hand, is passed along the path 3 to the patient's eye so as to provide uniform illumination around the slit illumination. As previously described, the intensity of the uniform illumination can be adjusted as desired by the iris 10a provided in the light guide element 10.

Figure 4:
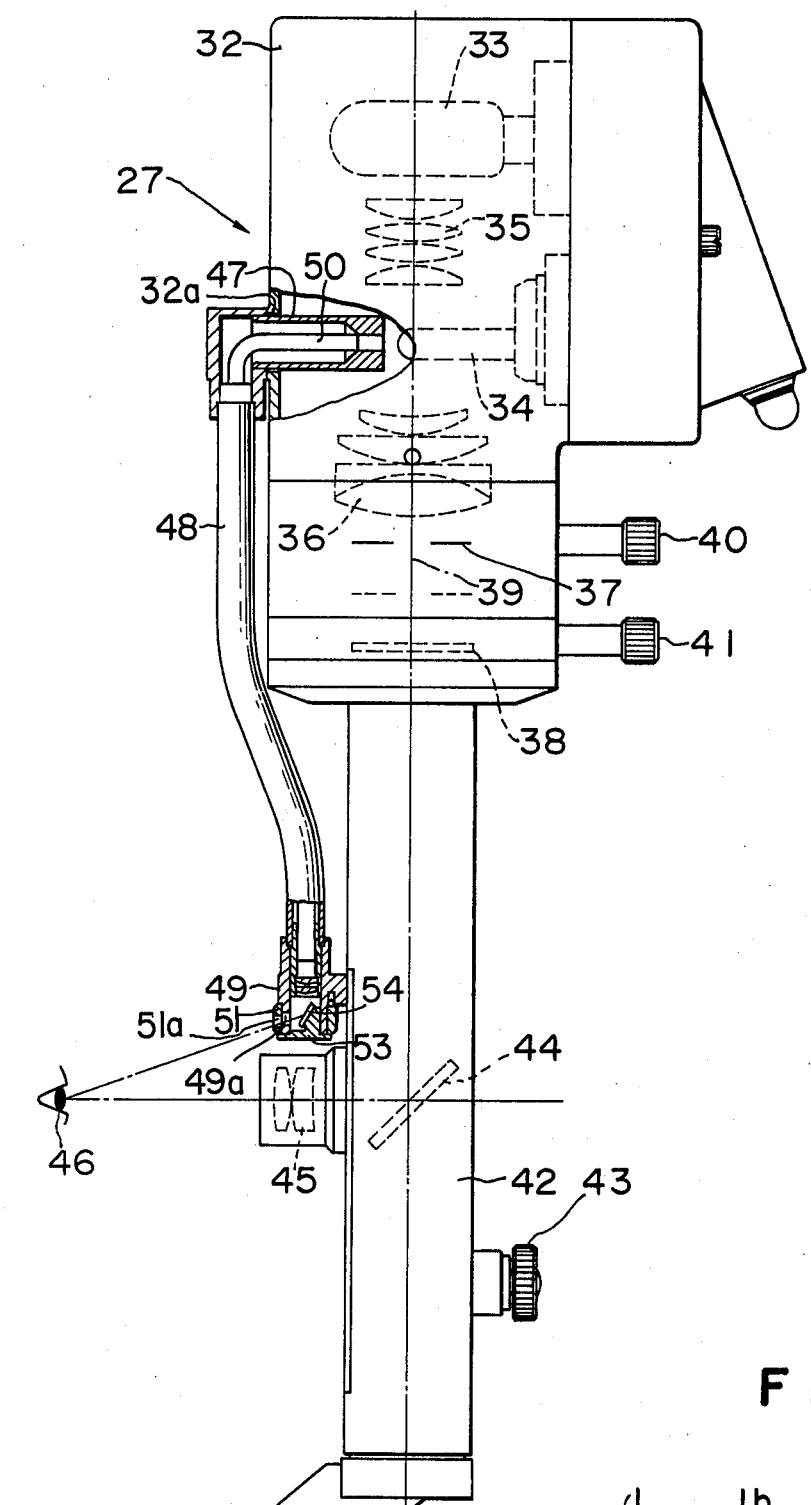

Referring now to FIGS. 3 and 4, the microscope shown therein includes a base 21 carrying a swingable support 22 which is mounted on the base 21 for swinging movement in a horizontal plane. The support 22 carries a photographing camera 23 having a microscopic lens 24 and an eye-piece 25 for visual investigation.

The base 21 further carries a second swingable support 26 which is mounted for swinging movement in a horizontal plane. The support 26 carries an illumination assembly 27 which will be described later in more detail.

A post 28 is secured to the base 21 and carries a chin rest 29 and a forehead rest 30 so as to fix the patient's head as shown in FIG. 3. A tube 31 is mounted on the post 28 and extends from the top end of the post 28 to the illumination assembly 27. Electric wires (not shown) are passed through the tube 31 to the illumination assembly 27 so as to provide a supply of electric power thereto.

Referring now to FIG. 4, the illumination assembly 27 includes a housing 32 for containing the light source means. More specifically, in the housing 32, there are disposed a light source 33, such as a tungsten lamp, and another light source 34, such as a xenon lamp. Between the lamps 33 and 34, there is provided a relay lens 35 in such a manner that the lamps 33 and 34 are conjugate with each other with respect to the relay lens 35.

In the housing, there is further disposed a condenser lens 36, an adjustable iris 37, and a slit mask 38 along the optical path 39. Adjusting knobs 40 and 41 are provided respectively for adjustments of the iris 37 and the slit mask 38.

The housing 32 has a downwardly extending hollow post portion 42 which is mounted on the swingable support 26 for rotation about a vertical axis and which is substantially in alignment with the optical axis 39. A manual knob 43 is provided on the post 42 for fixing the post 42 to the support 26 against rotation through an appropriate locking mechanism (not shown).

The optical path 39 extends along the axis of the post 42 and a mirror 44 is disposed in the post 42 for reflecting the light from the light source toward a projecting lens 45 provided on the post 42. Thus, the light from the lamp 33 or 34 is passed through the condenser lens 36, the iris 37, and the slit 38 along the optical axis 39, reflected by the mirror 44, and focused by the lens 45 on the patient's eye 46 in the form of a slit.

The housing 32 is formed at one side adjacent to the lamp 34 with an opening 32a where a L-shaped fitting 47 is secured. A hollow tube 48 extends downwardly from the fitting 47 to a second fitting 49 which is mounted on the post 42 at a position adjacent to the projecting lens 45.

In the fitting 47 and the tube 48, there is disposed an optical guide 50 in the form of a glass element having one end opposing the lamp 34 and the other end terminating at the fitting 49. The fitting 49 is provided at its side wall with a slot opening 49a, and carries a rotatable ring 51 having an opening 51a for co-operation with the slot opening 49a. The fitting 49 also carries a bottom closure 53 on which a reflecting mirror 54 is mounted for reflecting the light from the optical guide 50 toward and through the opening 51a so as to provide uniform illumination for the patient's eye 46.

The invention has thus been shown and described with reference to specific embodiments, however, it should be noted that the invention is in no way limited to the details of the illustrated structures but changes and modifications may be made without departing from the scope of the appended claims.

We claim:
1. A slit lamp microscope comprising:
   a first light source;
   means defining a first optical path, having slit means disposed therein, for directing light from said first light source to a patient's eye in the form of a slit;
   means defining a second optical path for directing light from said first light source to said patient's eye in the form of uniform illumination;
   a second light source;
   lens means interposed between said first and second light sources for directing light from said second light source along said first optical path;
   said second light source being disposed relative to said first light source such that the second light source does not interfere with the transmission of said light from said first light source along either of said first or second optical paths; and
   optical means defining a microscope for investigating said patient's eye.

2. A slit lamp microscope in accordance with claim 1 which further includes, in said first optical path, lens means for focusing the light, which has passed through the slit means, onto the patient's eye.

3. A slit lamp microscope in accordance with claim 1 which further includes photographing means for taking a picture of the patient's eye through the optical means.

4. Slit lamp microscope in accordance with claim 1 in which said second light path is constituted at least partially by optical guide means.

5. A slit lamp microscope as set forth in claim 1, wherein:
   said first light source is a xenon lamp having a pair of opposed electrodes disposed upon opposite sides of said first optical path; and
   said lens means is disposed along said first optical path so as to focus the light from said second light source at the gap defined between said paired electrodes,
   whereby the disposition of said first light source along said first optical path does not interfere with the transmission of said light from said second light source along said first optical path.

* * * * *

REEXAMINATION CERTIFICATE (608th)
United States Patent [19]
Takizawa et al.

[11] B1 4,102,565
[45] Certificate Issued Dec. 30, 1986

[54] SLIT LAMP MICROSCOPE

[75] Inventors: Shiro Takizawa, Tokyo; Shinicki Nishimura, Ageo, both of Japan

[73] Assignee: Tokyo Kogaku Kikai Kabushiki, Tokyo, Japan

Reexamination Request:
No. 90/000,691, Dec. 19, 1984

Reexamination Certificate for:
Patent No.: 4,102,565
Issued: Jul. 25, 1978
Appl. No.: 703,547
Filed: Jul. 8, 1976

[51] Int. Cl.⁴ .............................................. A61B 3/10
[52] U.S. Cl. .................................. 351/214; 351/221; 350/96.10

[56] References Cited

U.S. PATENT DOCUMENTS 3,068,745 12/1962 Peck .
3,414,348 12/1968 Gambs .
3,652,153 3/1972 Gambs .

FOREIGN PATENT DOCUMENTS 2460088 6/1976 Fed. Rep. of Germany .
131897 2/1938 Japan .
303574 5/1955 Japan .
4327694 9/1961 Japan .
4627590 9/1971 Japan .

OTHER PUBLICATIONS

Descriptive brochure in Japanese Language by Carl Zeiss, with English translation excerpts ("Zeiss").

*Primary Examiner*—Rodney B. Bovernick

[57] ABSTRACT

A slit lamp microscope includes an illumination light source from which light is passed through two separate optical paths to the patient's eye. The first of the optical paths includes a slit mask and a projecting lens so that the light is focused on the patient's eye to provide a bright slit-like illumination. The light which has passed through the second path provides a uniform auxiliary illumination around the illuminated slit area so that the location of the area can be readily determined with respect to other portions of the patient's eye.

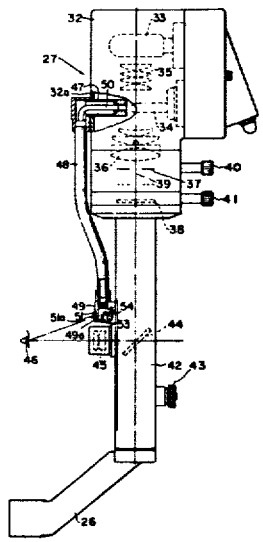

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-5 are cancelled.

* * * * *